(12) United States Patent
Brooks et al.

(10) Patent No.: US 6,218,345 B1
(45) Date of Patent: *Apr. 17, 2001

(54) CLEANSING COMPOSITIONS

(75) Inventors: Alan Brooks, Slough; Charles Marie Alain Du Reau, London, both of (GB)

(73) Assignee: The Procter & Gamble Company, Cincinnati, OH (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 31 days.

This patent is subject to a terminal disclaimer.

(21) Appl. No.: 09/214,194

(22) PCT Filed: Jul. 2, 1997

(86) PCT No.: PCT/US97/11679

§ 371 Date: Dec. 30, 1998

§ 102(e) Date: Dec. 30, 1998

(87) PCT Pub. No.: WO98/00499

PCT Pub. Date: Jan. 8, 1998

(30) Foreign Application Priority Data

Jul. 3, 1996 (GB) .................................................. 9613901

(51) Int. Cl.[7] .................................................. A61K 7/075
(52) U.S. Cl. .................... 510/123; 510/124; 510/125; 510/127; 510/137; 510/138; 510/139; 510/159; 510/473; 510/499; 510/502; 424/70.12; 424/70.13; 424/70.16; 424/70.19; 424/70.21; 424/70.22; 424/70.24; 424/70.31; 514/846
(58) Field of Search .................................. 510/123, 124, 510/125, 127, 137, 138, 139, 159, 473, 499, 502; 424/70.12, 70.13, 70.16, 70.19, 70.21, 70.22, 70.24, 70.31; 514/846

(56) References Cited

U.S. PATENT DOCUMENTS

| 5,318,728 | 6/1994 | Surutzidis et al. ................ 252/548 |
|---|---|---|
| 5,454,982 | 10/1995 | Murch et al. ........................ 252/548 |
| 5,489,393 | * 2/1996 | Connor et al. ....................... 510/237 |
| 5,905,062 | * 5/1999 | Elliott et al. ......................... 510/124 |
| 5,910,472 | * 6/1999 | Elliott et al. ......................... 510/124 |

FOREIGN PATENT DOCUMENTS

WO96/17917 * 6/1996 (WO) .

OTHER PUBLICATIONS

U.S. application No. 09/214,192, Brooks et al., filed Dec. 30, 1998.
U.S. application No. 09/214,204, Brooks et al., filed Dec. 30, 1998.
U.S. application No. 09/214,193, Brooks et al., filed Dec. 30, 1998.
U.S. application No. 09/215,205, Brooks et al., filed Dec. 30, 1998.
U.S. application No. 09/214,196, Brooks et al., filed Dec. 30, 1998.

* cited by examiner

Primary Examiner—Gregory R. Delcotto
(74) Attorney, Agent, or Firm—Lucy Elandjian; Darryl C. Little

(57) ABSTRACT

Personal cleansing compositions comprising a thickening system consisting essentially of hydrophobically modified water-soluble associative polymer and polar oil having a required HLB of at least 12, a nonionic polyhydroxy fatty acid amide surfactant, a water-soluble surfactant other than the polyhydroxy fatty acid amide surfactant, and water, wherein the polar oil has an average carbon chain length of from about 12 to about 16 carbon atoms and wherein the water-soluble surfactants have an average carbon chain of from about 10 to about 18 carbon atoms. These compositions may also comprise a perfume or cosmetic oil, or a hydrotrope.

The compositions of the present invention deliver excellent product thickening and rheological attributes, in storage, in dispensing and in use, in combination with good efficacy benefits such as excellent rinsibility, mildness, skin conditioning, skin moisturizing, product stability, cleansing and lathering.

23 Claims, No Drawings

CLEANSING COMPOSITIONS

TECHNICAL FIELD

The present invention relates to cleansing compositions. In particular it relates to mild personal cleansing compositions which display improved thickening and rheological properties in combination with good skin feel attributes, rinsing behaviour and foaming properties which are suitable for simultaneously cleansing and conditioning the skin and/or the hair and which may be used, for example, in the form of foam bath preparations, shower products, skin cleansers, hand, face and body cleansers, shampoos, etc.

BACKGROUND OF THE INVENTION

Mild cosmetic compositions must satisfy a number of criteria including cleansing power, foaming properties and mildness/low irritancy/good feel with respect to the skin, hair and the ocular mucosae. Skin is made up of several layers of cells which coat and protect the keratin and collagen fibrous proteins that form the skeleton of its structure. The outermost of these layers, referred to as the stratum corneum, is known to be composed of 250 Å protein bundles surrounded by 80 Å thick layers. Hair similarly has a protective outer coating enclosing the hair fibre which is called the cuticle. Anionic surfactants can penetrate the stratum corneum membrane and the cuticle and, by delipidization destroy membrane integrity. This interference with skin and hair protective membranes can lead to a rough skin feel and eye irritation and may eventually permit the surfactant to interact with the keratin and hair proteins creating irritation and loss of barrier and water retention functions.

Ideal cosmetic cleansers should cleanse the skin or hair gently, without defatting and/or drying the hair and skin and without irritating the ocular mucosae or leaving skin taut after frequent use. Most lathering soaps, shower and bath products, shampoos and bars fail in this respect.

Certain synthetic surfactants are known to be mild. However, a major drawback of most mild synthetic surfactant systems when formulated for shampooing or personal cleansing is poor lather performance compared to the highest shampoo and bar soap standards. Thus, surfactants that are among the mildest are marginal in lather. The use of known high sudsing anionic surfactants such as alkyl sulphates with lather boosters, on the other hand, can yield acceptable lather volume and quality but at the expense of clinical skin mildness. These two facts make the selection of suitable surfactants in the lather and mildness benefit formulation process a delicate balancing act.

In addition to the mildness, cleansing and lathering performance attributes desired by consumers it is important that personal cleansing products further have good thickening and rheological properties, in product storage, in dispensing and in-use.

It is known that water-soluble polymers can be used to provide desirable product thickening attributes and, furthermore, that hydrophobic modification of water-soluble polymers can improve their thickening efficacy. However, it is also known that the thickening properties of such hydrophobically modified water-soluble polymers can be significantly reduced in non-dilute, water-soluble surfactant systems (as discussed in Sau and Landoll 'Polymers in Aqueous Media', Advances in Chemistry Series No. 223, Chapters 8, 17, 18, edited by J. E. Glass). In particular, Applicant has found that in non-dilute, water-soluble surfactant systems, hydrophobically modified polymers, such as hydrophobically modified hydroxy ethyl cellulose, do not deliver good product thickening. Non-dilute, as defined herein, means systems comprising greater than about 1% by weight of water-soluble surfactant. Water-soluble, as defined herein, means a surfactant having a molecular weight of less than about 20,000 wherein the surfactant is capable of forming a clear, isotropic solution when dissolved in water at 0.2% w/w under ambient conditions (25° C.).

It is also well known that fatty alcohol ethoxylates and fatty alcohols can thicken systems containing both water-soluble surfactant and electrolyte (as illustrated, for example, in Hoechst Surfactants, published Trade Literature). However, fatty alcohol ethoxylates and fatty alcohols modify the micellar structure of the water-soluble surfactant system, resulting in undesirable effects on product characteristics such as the lather profile, rinsing behaviour and in-use product feel attributes. Applicant has also found, that, in order to achieve good product thickening in non-dilute, water-soluble surfactant systems via the exclusive use of a fatty alcohol ethoxylate and/or fatty alcohol thickening agent, the amount of fatty thickener required to deliver acceptable thickening attributes results in reduced lather and rinsing performance.

It is known that an additional difficulty associated with the use of fatty alcohol ethoxylate and/or fatty alcohol and electrolyte based thickening systems is that the thickening effect of such materials is highly dependant upon the purity and quality of the raw materials used. This can lead to unpredictability in thickening performance, such as thin products with non-recoverable low viscosity. This unpredictability makes it difficult to efficiently formulate systems using water-soluble surfactants which have predictable viscosity profiles when using these fatty materials.

In addition to the product thinning difficulties faced when attempting to thicken systems containing high levels of surfactant using fatty thickeners, applicant has found that mild, water-soluble nonionic surfactants, such as polyhydroxy fatty acid amides and alkyl polyglycosides are difficult to thicken using fatty thickeners and electrolyte based thickening systems.

Thus a need exists for effective thickening systems for mild, non-dilute, water-soluble surfactant systems comprising polyhydroxy fatty acid amide surfactants which deliver good product thickening and rheology attributes both in storage, in dispensing and in-use in combination with the delivery of excellent product characteristics such as lather, cleansing, rinsing, skin mildness and in-use skin feel attributres.

Applicant has found that personal cleansing compositions having excellent product thickening and rheology attributes, both under product storage and in-use conditions, are provided by the combination of a thickening system consisting essentially of associative polymer and polar oil in combination with polyhydroxy fatty acid amide surfactant and a non-dilute, water-soluble, auxiliary surfactant matrix.

SUMMARY OF THE INVENTION

The subject of the present invention is a mild, non-dilute, foam-producing, easily rinsed, cleansing products suitable for personal cleansing of the skin or hair which have good thickening and rheology properties and which may be used as shower products, skin cleansers and shampoos etc. According to one aspect of the invention, there is provided a liquid personal cleansing composition comprising:
(a) from about 0.01% to about 15% by weight of a thickening system which consists essentially of associative polymer and polar oil having a required HLB of at least 12.

(b) from about 0.1% to about 20% by weight of a nonionic polyhydroxy fatty acid amide surfactant having the general formula (III):

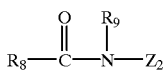

wherein $R_8$ is $C_5$–$C_{31}$ hydrocarbyl, $R_9$ is hydrogen, $C_1$–$C_8$ alkyl or hydroxyalkyl and $Z_2$ is a polyhydroxyhydrocarbyl moiety;

(c) from about 1% to about 60% by weight of water-soluble auxiliary surfactant other than the polyhydroxy fatty acid amide surfactant of (b), selected from anionic surfactant, nonionic, zwitterionic and amphoteric surfactants and mixtures thereof; and (d) water, wherein the average carbon chain length of the polar oil is from about 10 to about 18 carbon atoms and is substantially similar to the average carbon chain length of the combined polyhydroxy fatty acid amide and other surfactants in the water-soluble, non-dilute surfactant matrix.

In a highly preferred embodiment, the invention takes the form of a non-dilute, foam producing liquid cleansing composition having good product thickening and rheological properties.

All concentrations and ratios herein are by weight of the cleansing composition, unless otherwise specified. Surfactant chain lengths are also on a weight average chain length basis, unless otherwise specified.

DETAILED DESCRIPTION OF THE INVENTION

The liquid cleansing compositions herein combine a thickening system consisting essentially of associative polymer and polar oil in combination with polyhydroxy fatty acid amide surfactant and an auxiliary surfactant matrix and, optionally, polymeric skin conditioning agents. Preferred embodiments also contain perfume or cosmetic oils.

THICKENING SYSTEM

The liquid cleansing compositions herein are based on a thickening system consisting essentially of associative polymer, preferably hydrophobically modified water-soluble, nonionic polymer, and polar oil having a required HLB value of at least about 12, in combination with polyhydroxy fatty acid amide surfactant and an auxiliary water-soluble, non-dilute surfactant system, and optionally polymeric skin conditioning agents.

The total level of associative polymer and polar oil in the thickening system according to the present invention is from about 0.01% to about 15%, preferably about 0.01% to about 10%, more preferably from about 0.05% to about 8%, most preferably from about 0.1% to about 4%, especially from about 0.1% to about 2%, most especially from about 0.5% to about 1.5% by weight. The preferred ratio of associative polymer to polar oil is in the range of from about 1:5 to about 5:1, more preferably from about 1:3 to about 3:1, most preferably from about 1:2 to about 1:2.

The thickening system of the invention is valuable for the delivery of good product thickening and rheological attributes during product storage, dispensing and use.

A further benefit of the thickening systems of the present invention is that the product thickening is not dependant of the presence of electrolyte in the surfactant matrix. Thus, it is now possible to formulate a non-dilute, water-soluble surfactant matrix having desirable product thickening and rheological attributes without the use of an electrolyte.

Applicant has found that this independence from electrolyte is particularly valuable for the delivery of desirable thickening properties when formulating mild, non-dilute, water-soluble surfactant systems comprising polyhydroxy fatty acid amide surfactants (as discussed hereinafter).

Associative Polymers

The thickening systems of the present invention contain, as an essential component, an associative polymer at a level of from about 0.01% to about 12%, preferably from about 0.01% to about 10%, more preferably from about 0.05% to about 8%, most preferably from about 0.1% to about 4%, especially from about 0.1% to about 2%, most especially from about 0.5% to about 1.5% by weight. Associative polymers are valuable, in the compositions herein, in combination with polar oils having a required HLB of at least 12, for the delivery of good product thickening and rheological attributes in non-dilute, water-soluble surfactant systems comprising polyhydroxy fatty acid amide and auxiliary surfactants.

In the compositions according to the present invention preferred associative polymers are nonionic associative polymers having an average molecular weight in the range of from about 2,000 to about 2,000,000, preferably from about 10,000 to about 1,000,000, more preferably from about 20,000 to about 800,000.

Associative polymers are a subclass of water-soluble polymers and are generally water-soluble macromolecular structures having of both hydrophilic and hydrophobic components. Associative polymers can thicken surfactant solutions predominantly via intermolecular association between the water-insoluble hydrophobic components on the water-soluble polymer backbone (discussed in detail by G. D. Shay in Polymers in Aqueous Media, Advances in Chemistry series 223, pp467. Edited by J. E. Glass).

As discussed in herein before, associative thickeners are known to build viscosity in the presence of low levels of water-soluble surfactants (i.e., less than about 1% w/w), as described in EP-A-0,412,706, and the literature reports on the interaction of such associative thickeners with specific surfactants (Sau and Landoll, 'Polymers in Aqueous Media', Advances in Chemistry Series No. 223, pp 343–364, Edited by J. E. Glass).

Hydrophobically modified polymer, as defined herein, means, a water soluble (hydrophilic) associative polymer which has been modified by the addition of hydrophobic groups to enhance its thickening potential (as discussed in Sau and Landoll 'Polymers in Aqueous Media', Advances in Chemistry Series No. 223, Chapters 8, 17, 18, edited by J. E. Glass). The generally accepted model of product thickening, in terms of hydrophobically modified water-soluble nonionic polymers, is that thickening results from intermolecular association between the hydrophobic groups on the polymer (Sau and Landoll, 'Polymers in Aqueous Media', Advances in Chemistry Series No. 223, pp 343–364, edited by J. E. Glass). In particular, the effect of simple anionic surfactant, e.g. SDS, and nonionic surfactant, e.g. CxEy, on hydrophobically modified hydroxy ethyl cellulose HMHEC) (as discussed in Sau & Landoll in 'Polymers in Aqueous Media', Advances in Chemistry Series No. 223, pp 343–364 and Tanaka et al. in Macromolecules, 1992, 25, pp 1304–1310) and hydrophobically modified ethoxy urethane (HEUR) (Hulden, Colloids & Surfaces, 82 (1994), 263–277).

Preferred liquid cleansing compositions herein are based on a thickening system consisting essentially of hydrophobically modified water-soluble, nonionic polymer and polar oil having a required HLB value of at least about 12, in combination with a water-soluble, non-dilute surfactant system comprising polyhydroxy fatty acid amide and auxiliary surfactants, and optionally polymeric skin conditioning agents. Water-soluble, in terms of hydrophobically modified water-soluble nonionic polymer, as defined herein, means, polymer having at least a water-soluble backbone and/or linkages.

While not wishing to be bound to any particular theory, it is proposed herein that the hydrophobically modified water-soluble nonionic polymer and polar oil thickeners of the present invention, interact, in the presence of non-dilute, water-soluble surfactant systems comprising polyhydroxy fatty acid amide and auxiliary surfactants to deliver excellent product thickening characteristics.

Hydrophobically modified water-soluble nonionic polymers suitable for use in the thickening systems of the present invention include hydrophobically modified hydroxyalkyl cellulose polymers such as hydrophobically modified hydroxyethyl cellulose (HMHEC), hydrophobically modified alkoxylated urethane polymers, such as hydrophobically modified ethoxylated urethane (HEUR), and hydrophobically modified nonionic polyols.

Hydrophobically Modified Hydroxyalkyl Cellulose Thickener

Cellulose ethers suitable for use herein, have, prior to hydrophobic modification, a sufficient degree of nonionic substitution selected from methyl, ethyl, hydroxyethyl and hydroxypropyl to cause them to be water-soluble. The preferred degree of nonionic substitution is in the range of from about 1.8 to about 4.0, preferably from about 2 to about 3, and especially from about 2.2 to about 2.8 by weight. The cellulose ethers are then further substituted with alkyl or alkenyl groups having from about 10 to about 24, preferably from about 14 to about 18 carbon atoms in an amount of from about 0.1 to about 1, preferably from about 0.3 to about 0.8, and especially from about 0.4 to about 0.6 weight percent. The cellulose ether to be modified is preferably one of low to medium molecular weight, i.e., less than 800,000 and preferably between 20,000 and 700,000 (75 to 2500 D.P.). Degree of polymerisation (D.P.) as defined herein, means, the average number of glycoside units in the polymer.

Preferred cellulose ethers for use herein are selected from commercially available nonionic cellulose ethers such as hydroxy ethyl cellulose, hydroxy propyl methyl cellulose, hydroxy methyl cellulose, ethyl hydroxy ethyl cellulose and mixtures thereof.

The preferred cellulose ether substrate, for use herein, is a hydroxyethyl cellulose (HEC) of from about 50,000 to about 700,000 molecular weight. Hydroxyethyl cellulose of this molecular weight level is the most hydrophilic of the materials completed. Accordingly, control of the modification process and control of the properties of the modified product can be more precise with this substrate. Hydrophilicity of the most commonly used nonionic cellulose ethers varies in the general direction: hydroxyethyl>hydroxypropyl>hydroxypropyl methyl>methyl.

The long chain alkyl modifier, for the cellulose ether, can be attached to the cellulose ether substrate via an ether, ester or urethane linkage. The ether linkage is preferred. Although the modified cellulose ether materials are referred to as being "alkyl modified", (the term alkyl as used generally herein also includes using alkenyl) it will be recognised that except in the case where modification is effected with an alkyl halide, the modifier is not a simple long chain alkyl group. The group is actually an alphahydroxyalkyl radical in the case of an epoxide, a urethane radical in the case of an isocyanate, or an acyl radical in the case of an acid or acyl chloride. General methods for making modified cellulose ethers are taught in Landoll ('277) at column 2, lines 36–65.

Highly preferred hydrophobically modified hydroxy ethyl cellulose (HMHEC) polymers suitable for use herein have a 1% aqueous viscosity in the range of from about 8,000 to about 50,000 mPas (Brookfield LVT viscometer, spindle No. 4, speed 4).

Commercially available materials preferred for use herein include NATROSOL PLUS Grade 330 CS (TM), a hydrophobically modified hydroxyethylcellulose available from Aqualon Company, Wilmington, Del. This material has a $C_{16}$ alkyl substitution of from 0.4% to 0.8% by weight. The hydroxyethyl molar substitution for this material is from 3.0 to 3.7. The average molecular weight for the water-soluble cellulose prior to modification is approximately 300,000. Also suitable for use herein is NATROSOL PLUS Grade 430 CS (TM).

Another material of this type is sold under the trade name NATROSOL PLUS CS Grade D-67 (TM), by Aqualon Company, Wilmington, Del. This material has a $C_{16}$ substitution of from 0.50% to 0.95%, by weight. The hydroxyethyl molar substitution for this material is from 2.3 to 3.7. The average molecular weight for the water soluble cellulose prior to modification is approximately 700,000. Highly preferred for use herein are $C_{14}$–$C_{18}$ alkyl and alkenyl modified hydroxy ethyl cellulose polymers having a degree of ethoxylation of from about 1.8 to about 3.2, preferably from about 2.0 to about 3.0, more preferably from about 2.2 to about 2.8 and an alkyl and alkenyl substitution level of from about 0.3 to about 0.8, preferably from about 0.4 to about 0.7, most preferably from about 5.5 to about 0.7 and especially about 0.65. Highly preferred are cetyl modified hydroxy ethyl cellulose polymers as available from the Aqualon Co. under the trade names Polysurf 67 (TM) having a molecular weight of about 700,000.

Hydrophobically Modified Alkoxylate Urethane Thickener

Hydrophobically modified water-soluble nonionic alkoxylated urethane polymers suitable for use herein are particularly valuable for providing excellent stability characteristics over normal temperature ranges (5° C. to about 50° C.) as well as delivering near Newtonian rheology behaviour at low shear rates in matrices comprising high surfactant levels, and for delivery of improved product thickening characteristics and rheological behaviour in combination with polar oil, having a required HLB of at least 12, in a water-soluble, non-dilute surfactant system comprising polyhydroxy fatty acid amide and auxiliary surfactants.

Hydrophobically modified water-soluble nonionic alkoxylated urethane polymers are made by prepolymerisation of a diisocyanate with a polyol followed by end capping with primary amines or primary alcohols. The resulting molecule is usually a linear block copolymer, with internal and terminal hydrophobes but branched and cross linked polymer can also be obtained.

The polymerisation process is very complex and various resulting polymer structures can be formed as reviewed in the literature by Hulden (Colloids & Surfaces, 82, 263–277), Kaczmarski et al. (Polym. Mater. Sci. Eng., 67, 282–283), and Karunasena et al. (Polymers in aqueous media, Advances in Chemistry Series, 223, 495–525). Further details on hydrophobically modified water-soluble nonionic alkoxylated urethane polymers as thickeners are discussed in the paper titled 'Polymers in Cosmetics', presented by Rohm & Haas as part of 'The Proceedings of the 20th National Congress of the Society of Italian Cosmetic Chemists 1993' at p29.

Preferred hydrophobically modified water-soluble nonionic alkoxylated urethane polymers for use herein are described by Kaczmarski et al. as linear block copolymers (which can be obtained by a step—growth process) and can have the following general structures:

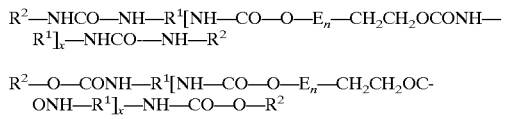

wherein: $E_n$ is a polyol having the general formula, $(CH_2CH_2O)_n$, n can vary from 10 to 10,000, preferably from 10 to 1,000, and more preferably from 50 to 500; $R^1$ includes straight or branched chain alkyl, alkenyl or aromatic groups containing pending functional groups e.g. COOH; $R^2$ includes straight or branched chain alkyl, alkenyl or aromatic groups containing pending functional groups e.g. COOH and wherein $R^2$ is preferably selected from $NH_2$ or OH and wherein x represents the degree of polymerisation.

Preferred hydrophobically modified water-soluble nonionic alkoxylated urethane polymers suitable for use herein are those sold by Rohm & Haas under Acrysol 44 (TM), by Berol Nobel under Bermodol 2101 (TM), 2130 (TM) and Bermodol Pur 2100 (TM) and by Servo under the name Ser-Ad-FX-100 (TM).

Hydrophobically Modified Nonionic Polyols

Also suitable for use herein as thickeners are hydrophobically modified water-soluble nonionic polyols. Suitable hydrophobically modified water-soluble nonionic polyols for use herein are fatty acid esters of glucosides such as PEG 120 methyl glucoside dioleate (available from Amercol under the trade name Glucamate DOE 120), PEG-150 pentaerythrityl tetrastearate (available from Croda under the trade name Crothix (TM)), PEG-75 dioleate (available from Kessco under the trade name PEG-4000 dioleate (TM)) and PEG-150 distearate (available from Witco under the trade name Witconal L32 (TM)).

Polar Oil

A further essential feature of the thickening systems of the present invention is polar oil having a required HLB of at least 12. Polar oil is present in the cleansing compositions herein at a level of from about 0.01% to about 3%, preferably from about 0.01% to about 2%, more preferably from about 0.1% to about 1%, most preferably from about 0.2% to about 0.8% by weight.

Polar oil as defined herein, means, an organic oil, in liquid or waxy form, having one or more hydrophilic or polar functionalities, and which, can interact with associative polymer, in the presence of a water-soluble, non-dilute surfactant system comprising polyhydroxy fatty acid amide and auxiliary surfactants to deliver excellent product thickening and rheology attributes.

Polar oils suitable for use as thickeners herein have a required HLB value of about at least 12, preferably from about 12 to about 15, more preferably from about 12 to about 14. Required HLB value, as defined herein, represents the "Required Hydrophile/Lipophile Balance" and can be assessed by the standard technique well known in the art.

The HLB concept in general, and specifically the required HLB, is also described more fully in "The HLB System", published by ICI Americas Inc., Wilmington, Del.

Exemplary polar oils suitable for use in the compositions according to the present invention include and synthetic fatty alcohols and fatty acids having an average carbon chain length of from about 10 to 18 carbon atoms. Fatty alcohols suitable for use herein include decyl alcohol, lauryl alcohol, cetyl alcohol, stearyl alcohol and mixtures thereof. Additional polar oils include fatty acids having an average carbon chain length of from about 12 to 16 carbon atoms, such as lauric acid and myristic acid.

Applicant has also found that the carbon chain length of the polar oil has an impact on the degree of product thickening delivered to water-soluble, non-dilute surfactant systems comprising polyhydroxy fatty acid amide and auxiliary surfactants by the thickening systems of the present invention. In general, preferred polar oils suitable for use herein have an average carbon chain length which is in the range of from about 10 to about 18, preferably from about 12 to about 16 and especially from about 12 to about 14 carbon atoms. Particularly preferred for use herein are systems wherein the average carbon chain length of the polar oil is substantially similar to the average carbon chain length of the water-soluble, non-dilute surfactant system comprising polyhydroxy fatty acid amide and auxiliary surfactants. Substantially similar average carbon chain length, as defined herein, means, carbon chain lengths within two, preferably one, carbon units difference, i.e, $C_{12}$ is defined herein as substantially similar to $C_{14}$.

Polar oils having an average carbon chain length of from about 12 to about 14 carbon atoms on the alkyl chain are preferred in the cleansing compositions according to the invention, as surfactants having an average carbon chain length of from about 12 to about 14 carbon atoms are highly desirable for the delivery of good foaming properties.

As herein before discussed, particularly suitable for use in the thickening system of the present invention are polar oils having a chain length substanitally similar to that of the chosen surfactant system. Preferred polar oils for use herein are $C_{12}$ to $C_{14}$ alcohols such as Lauryl Alcohol (Laurex NC (RTM) from Albright & Wilson), $C_{12}$ to $C_{13}$ alcohols (Dobanol 23 from Shell UK) and $C_{12}$ to $C_{15}$ alcohols Dobanol 25 from Shell UK) and , $C_{14}$ to $C_{15}$ alcohols (Dobanol 45 from Shell UK) also available under the Neodol trademark from Shell US Inc.

Applicant has also found that the level of polar oil thickener present in the thickening system of the invention has a finite effect on the increase in product thickening (i.e., as the level of polar oil increases, relative to the total surfactant level, the degree of thickening achieved in the surfactant matrix eventually reaches a plateau).

The present compositions can also comprise an auxiliary nonionic or anionic polymeric thickening component, especially a water-soluble polymeric materials, having a molecular weight greater than about 20,000. By "water-soluble polymer" is meant that the material will form a substantially clear solution in water at a 1% concentration at 250° C. and the material will increase the viscosity of the water. Examples of water-soluble polymers which may desirably be used as an additional thickening component in the present compositions, are hydroxyethylcellulose, hydroxypropyl cellulose, hydroxypropyl methylcellulose, polyethylene glycol, polyacrylamide, polyacrylic acid, polyvinyl alcohol (examples include PVA 217 from Kurary Chemical Co., Japan), polyvinyl pyrrolidone K-120, dextrans, for example Dextran purified crude Grade 2P, available from D&O Chemicals, carboxymethyl cellulose, plant exudates such as acacia, ghatti, and tragacanth, seaweed extracts such as sodium alginate, propylene glycol alginate and sodium carrageenan. Preferred as the additional thickeners for the present compositions are natural polysaccharide materials. Examples of such materials are guar gum, locust bean gun, and xanthan gum. Also suitable herein preferred is hydroxyethyl cellulose having a molecular weight of about 700,000.

Polyhydroxy Fatty Acid Amide Surfactant

The compositions according to the present invention comprise, as an essential feature, a mild water-soluble polyhydroxy fatty acid amide nonionic surfactant at levels of from about 0.1% to about 20%, more preferably from about 0.1% to about 10%, and especially from about 1% to about 8% by weight. Suitable for use herein are polyhydroxy fatty acid amide surfactants having the general formula (III).

The preferred N-alkyl, N-alkoxy or N-aryloxy, polyhydroxy fatty acid amide surfactants according to formula (III) are those in which $R_8$ is $C_5$–$C_{31}$ hydrocarbyl, preferably $C_6$–$C_{19}$ hydrocarbyl, including straight-chain and branched chain alkyl and alkenyl, or mixtures thereof and $R_9$ is typically, hydrogen, $C_1$–$C_8$ alkyl or hydroxyalkyl, preferably methyl, or a group of formula —$R^1$—O—$R^2$ wherein $R^1$ is $C_2$–$C_8$ hydrocarbyl including straight-chain, branched-chain and cyclic (including aryl), and is preferably $C_2$–$C_4$ alkylene, $R^2$ is $C_1$–$C_8$ straight-chain, branched-chain and cyclic hydrocarbyl including aryl and oxyhydrocarbyl, and is preferably $C_1$–$C_4$ alkyl, especially methyl, or phenyl. $Z_2$ is a polyhydroxyhydrocarbyl moiety having a linear hydrocarbyl chain with at least 2 (in the case of glyceraldehyde) or at least 3 hydroxyls (in the case of other reducing sugars) directly connected to the chain, or an alkoxylated derivative (preferably ethoxylated or propoxylated) thereof. $Z_2$ preferably will be derived from a reducing sugar in a reductive ammination reaction, most preferably $Z_2$ is a glycityl moiety. Suitable reducing sugars include glucose, fructose, maltose, lactose, galactose, mannose, and xylose, as well as glyceraldehyde. As raw materials, high dextrose corn syrup, high fructose corn syrup, and high maltose corn syrup can be utilised as well as the individual sugars listed above. These corn syrups may yield a mix of sugar components for $Z_2$. It should be understood that it is by no means intended to exclude other suitable raw materials. $Z_2$ preferably will be selected from the group consisting of —$CH_2$—$(CHOH)_n$—$CH_2OH$, —$CH(CH_2OH)$—$(CHOH)_{n-1}$—$CH_2H$, $CH_2(CHOH)_2(CHOR')CHOH)$—$CH_2OH$, where n is an integer from 1 to 5, inclusive, and R' is H or a cyclic mono- or poly-saccharide, and alkoxylated derivatives thereof. As noted, most preferred are glycityls wherein n is 4, particularly —$CH_2$—$(CHOH)_4$—$CH_2OH$.

The most preferred polyhydroxy fatty acid amide has the formula $R_8(CO)N(CH_3)CH_2(CHOH)_4CH_2OH$ wherein $R_8$ is a $C_6$–$C_{19}$ straight chain alkyl or alkenyl group. In compounds of the above formula, $R_8$—CO—N< can be, for example, cocoamide, stearamide, oleamide, lauramide, myristamide, capricamide, palmiamide, tallowamide, etc.

A preferred process for making the above compounds having formula (III) comprises reacting a fatty acid triglyceride with an N-substituted polyhydroxy amine in the substantial absence of lower ($C_1$—$C_4$) alcoholic solvent, but preferably with an alkoxylated alcohol or alkoxylated alkyl phenol such as NEODOL and using an alkoxide catalyst at temperatures of from about 50° C. to about 140° C. to provide high yields (90–98%) of the desired products. Suitable processes for making the desired polyhydroxy fatty acid amide compounds are outlined in U.S. Pat. No. 5,194,639 and U.S. Pat. No. 5,380,891.

It is known that mild, nonionic surfactants such as polyhydroxy fatty acid amides and alkyl polyglycosides can deliver excellent skin mildness characteristics in combination with good lather and cleansing attributes. However, Applicant has found that auxiliary, water-soluble, non-dilute surfactant system comprising polyhydroxy fatty acid amide and auxiliary surfactants at high (>1% w/w) levels can be relatively unresponsive or unstable in the presence of conventional thickening agents, such as electrolyte. For example, when improperly formulated, non-dilute, auxiliary, water-soluble surfactant systems comprising polyhydroxy fatty acid amide surfactants and electrolyte are water-thin and difficult to thicken.

In addition to the product thinning and stability limitations of such conventional thickening agents, Applicant has also found that incorporation of alternative thickening agents, such as hydroxy ethyl cellulose, xanthan gum, guar gum, polymer JR 30M (TM), into non-dilute, water-soluble surfactant matrices comprising polyhydroxy fatty acid amide surfactant can provide some thickening but at the expense of lather and rinsing performance.

Thus, it would be desirable to develop a thickening system for the formulation of mild, non-dilute, water-soluble surfactant systems comprising polyhydroxy fatty acid amide and/or alkyl polyglycoside which deliver good product thickening, rheology and stability attributes in combination with good lather and rinsing performance.

Applicant has now found that the thickening system of the present invention is valuable for the delivery of excellent product thickening and rheology attributes in combination with good lather performance and skin mildness attributes in non-dilute, water-soluble surfactant systems comprising mild polyhydroxy fatty acid amide and water-soluble auxiliary surfactants.

According to another aspect of the invention there is provided a personal cleansing composition comprising:

(a) from about 0.01% to about 15% by weight of a thickening system which consists essentially of associative polymer and polar oil having a required HLB of at least 12.

(b) from about 0.1% to about 20% by weight of a nonionic polyhydroxy fatty acid amide surfactant having the general formula (III):

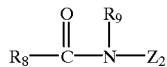

wherein $R_8$ is $C_5$–$C_{31}$ hydrocarbyl, $R_9$ is hydrogen, $C_1$–$C_8$ alkyl or hydroxyalkyl and $Z_2$ is a polyhydroxyhydrocarbyl moiety;

(c) from about 1% to about 60% by weight of water-soluble auxiliary surfactant other than the polyhydroxy fatty acid amide surfactant of (b), selected from anionic surfactant, nonionic, zwitterionic and amphoteric surfactants and mixtures thereof; and (d) water.

wherein the average carbon chain length of the polar oil is from about 10 to about 18 carbon atoms and is substantially similar to the average carbon chain length of the combined polyhydroxy fatty acid amide and other mild surfactants in the water-soluble, non-dilute surfactant matrix.

Auxiliary Surfactant System

As a further essential feature the compositions of the present invention comprise an auxiliary water-soluble, non-dilute surfactant system comprising polyhydroxy fatty acid amide and auxiliary surfactants. Water-soluble, as defined herein, means a surfactant having a molecular weight of less than about 20,000 wherein the surfactant is capable of forming a clear isotropic solution when dissolved in water at 0.2% w/w under ambient conditions. Surfactants suitable for inclusion in compositions according to the present invention generally have a lipophilic chain length of from about 8 to about 22 carbon atoms and can be selected from anionic, nonionic, zwitterionic and amphoteric surfactants and mixtures thereof. The total level of surfactant is preferably from about 2% to about 40%, more preferably from about 3% to about 15% by weight. The compositions preferably comprise a mixture of anionic with zwitterionic and/or amphoteric surfactants. The level of the individual anionic, zwitterionic and amphoteric surfactant components, where present, is in the range from about 1% to about 15%, and especially from about 1% to about 10% by weight of the composition, while the level of nonionic surfactant, where present, is in the range from about 0.1% to about 20% by weight, preferably from about 0.5% to about 16%, more preferably from about 1% to about 12% by weight. The weight ratio of anionic surfactant: zwitterionic and/or amphoteric surfactant is in the range from about 1:10 to about 10:1, preferably from about 1:5 to about 5:1, more preferably from about 1:3 to about 3:1. Other suitable compositions within the scope of the invention comprise mixtures of anionic, zwitterionic and/or amphoteric surfactants with one or more nonionic surfactants. Preferred for use herein are soluble or dispersible nonionic surfactants selected from ethoxylated animal and vegetable oils and fats and mixtures thereof, sometimes referred to herein as "oil-derived" nonionic surfactants.

The compositions of the invention can comprise an auxiliary, water-soluble anionic surfactant at levels from about 0.1% to about 20%, more preferably from about 0.1% to about 10%, and especially from about 1% to about 8% by weight.

Water-soluble auxiliary anionic surfactants suitable for inclusion in the compositions of the invention can generally be described as mild synthetic detergent surfactants and include alkyl sulphates, ethoxylated alkyl sulfates, alkyl ethoxy carboxylates, alkyl glyceryl ether sulfonates, methyl acyl taurates, fatty acyl glycinates, N-acyl glutamates, acyl isethionates, alkyl sulfosuccinates, alkyl ethoxysulphosuccinates, alpha-sulfonated fatty acids, their salts and/or their esters, alkyl phosphate esters, ethoxylated alkyl phosphate esters, alkyl sulphates, acyl sarcosinates and fatty acid/protein condensates, and mixtures thereof. Alkyl and/or acyl chain lengths for these surfactants are $C_{12}$–$C_{22}$, preferably $C_{12}$–$C_{18}$ more preferably $C_{12}$–$C_{14}$.

Surfactants of this class include short-chain alkyl sulphate surfactants where 'short chain' as defined herein means an average carbon chain length of $C_{10}$ or less. The short chain alkyl sulphate surfactants of the present invention are valuable in shower gel compositions for the delivery of improved skin mildness attributes and product rinsing benefits in combination with a desirable lather profile. Alkyl sulphate surfactants suitable for inclusion in the compositions of the present invention have the general formula (II);

R—SO$_3$—M wherein R is straight or branched chain alkyl, preferably straight chain, containing on average from about 8 to about 10 carbon atoms, preferably about 10 carbon atoms and wherein M is selected from alkali metals, ammonium or other suitable monovalent cation or mixtures thereof. It should be understood that the definition of any particular carbon chain length, say $C_8$ is an average value and as such may contain certain proportions of both higher and lower carbon chain lengths as a direct function of its synthesis. The level of such material can be achieved by modification of the process and the nature of the starting materials. While $C_{10}$ alkyl sulphate is the preferred surfactant in the compositions of the invention mixtures of short chain alkyl sulphates may also be used. Especially preferred in the compositions herein is $C_{10}$ alkyl sulphate material containing at least about 80% by weight of the $C_{10}$, preferably at least about 90% $C_{10}$, more preferably at least about 95% $C_{10}$ and especially at least about 99% $C_{10}$ alkyl sulphate. Suitable short chain alkyl sulphate materials are available from Albright and Wilson under the trade names Empicol LC35 and Empicol 0758F.

Additional auxiliary, water-soluble anionic surfactants suitable for use in the compositions according to the present invention are the salts of sulfuric acid esters of the reaction product of I mole of a higher fatty alcohol and from about 1 to about 12 moles of ethylene oxide, with sodium, ammonium and magnesium being the preferred counterions. Particularly preferred are the alkyl ethoxy sulphates containing from about 2 to 6, preferably 2 to 4 moles of ethylene oxide, such as sodium laureth-2 sulphate, sodium laureth-3 sulphate and magnesium sodium laureth-3.6 sulphate. In preferred embodiments, the anionic surfactant contains at least about 50% especially at least about 75% by weight of ethoxylated alkyl sulphate.

In addition to the broad range ethoxylated alkyl sulphates obtained via conventional sodium catalysed ethoxylation techniques and subsequent sulphation processes, ethoxylated alkyl sulphates obtained from narrow range ethoxylates (NREs) are also suitable auxiliary, water-soluble anionic surfactants for use in the present compositions. Narrow range ethoxylated alkyl sulphates suitable for use herein are selected from sulphated alkyl ethoxylates containing on average from about 1 to about 6, preferably from about 2 to about 4 and especially about 3 moles of ethylene oxide such as NRE sodium laureth-3 sulphate. NRE materials suitable for use herein contain distributions of the desired ethylene oxide $EO_n$) in the ranges of from 15% to about 30% by weight of $EO_n$, from about 10% to about 20% by weight of $EO_{n+1}$ and from about 10% to about 20% by weight of $EO_{n-1}$. Highly preferred NRE materials contain less than about 9% by weight of ethoxylated alkyl sulphate having 7 or more moles of ethylene oxide and less than about 13% by weight of non-ethoxylated alkyl sulphate. Suitable laureth 3 sulphate NRE materials are available from Hoechst under the trade names GENAPOL ZRO Narrow Range and GENAPOL Narrow Range.

The compositions of the present invention may contain, as an auxiliary water-soluble anionic surfactant alkyl ethoxy carboxylate surfactant at a level of from about 0.5% to about 15%, preferably from about 1% to about 10%, more preferably from about 1% to about 6% and especially from about 1% to about 4% by weight. Alkyl ethoxy carboxylate surfactant is particularly valuable in the compositions according to the present invention for the delivery of excellent skin mildness attributes in combination with excellent rinsing performance and desirable lather characteristics.

Alkyl ethoxy carboxylates suitable for use herein have the general formula (I):

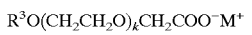
R$^3$O(CH$_2$CH$_2$O)$_k$CH$_2$COO$^-$M$^+$ wherein $R^3$ is a $C_{10}$ to $C_{15}$ alkyl or alkenyl group, preferably a $C_{11}$–$C_{15}$, more preferably a $C_{12}$–$C_{14}$ alkyl or $C_{12}$–$C_{13}$ alkyl group, k is an average value of ethoxylation ranging from 2 to about 7, preferably from about 3 to about 6, more preferably from about 3.5 to about 5.5, especially from about 4 to about 5, most preferably from about 4 to about 4.5, and M is a water-solubilizing cation, preferably an alkali metal, alkaline earth metal, ammonium, lower alkanol ammonium, and mono-, di-, and tri-ethanol ammonium, more preferably sodium, potassium and ammonium, most preferably sodium and ammonium and mixtures thereof with magnesium and calcium ions.

Particularly preferred as auxiliary, water-soluble anionic surfactants suitable for use herein are alkyl ethoxy carboxylate surfactants having a selected distribution of alkyl chain length and/or ethoxylate. Thus, the alkyl ethoxy carboxylate surfactants suitable for use in the compositions according to the present invention may comprise a distribution of alkyl ethoxy carboxylates having different average values of $R^3$ and/or k.

The average value of k will generally fall in the range of from about 3 to about 6 when the average $R^3$ is $C_{11}$, $C_{12}$, $C_{13}$ or $C_{14}$. Preferred auxiliary, water-soluble anionic alkyl ethoxy carboxylate surfactants suitable for use herein are the $C_{12}$ to $C_{14}$ (average EO 3-6) ethoxy carboxylates and the $C_{12}$ to $C_{13}$ (average EO 3-6) ethoxy carboxylates. Suitable materials include salts of NEODOX 23-4 (RTM) available from Shell Inc. (Houston, Tex., U.S.A.). Highly preferred for use herein are alkyl ethoxy carboxylate surfactants wherein, when $R^3$ is a $C_{12}$–$C_{14}$ or $C_{12}$–$C_{13}$ alkyl group and the average value of k is in the range of from about 3 to about 6, more preferably from about 3.5 to about 5.5, especially from about 4 to about 5 and most preferably from about 4 to about 4.5.

The compositions according to the present invention may additionally comprise auxiliary water-soluble nonionic surfactant, other than polyhydroxy fatty acid amides as described herein before, at levels from about 0.1% to about 20%, more preferably from about 0.1% to about 10%, and especially from about 1% to about 8% by weight. Surfactants of this class include $C_{12}$–$C_{14}$ fatty acid mono-and dialkanolamides such as cocoethanolamide, cocomonoisopropylamide, cocodiethanolamide and ethoxylated derivatives thereof, sucrose polyester surfactants and $C_{10}$–$C_{18}$ alkyl polyglycosides.

The compositions for use herein may also contain a auxiliary, water-soluble amphoteric surfactant. Amphoteric surfactants suitable for use in the compositions of the invention include:

(a) imidazolinium surfactants of formula (IV)

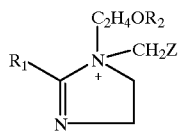

wherein $R_1$ is $C_7$–$C_{22}$ alkyl or alkenyl, $R_2$ is hydrogen or $CH_2Z$, each Z is independently $C_2M$ or $CH_2CO_2M$, and M is H, alkali metal, alkaline earth metal, ammonium or alkanolammonium; and/or ammonium derivatives of formula (V)

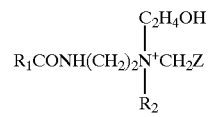

wherein $R_1$, $R_2$ and Z are as defined above;

(b) aminoalkanoates of formula (VI)

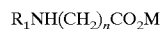

iminodialkanoates of formula (VII)

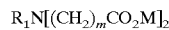

and iminopolyalkanoates of formula (VIII)

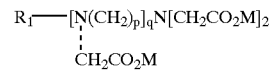

wherein n, m, p, and q are numbers from 1 to 4, and $R_1$ and M are independently selected from the groups specified above; and (c) mixtures thereof Suitable amphoteric surfactants of type (a) are marketed under the trade name Miranol and Empigen and are understood to comprise a complex mixture of species. Traditionally, the Miranols have been described as having the general formula IV, although the CTFA Cosmetic Ingredient Dictionary, 3rd Edition indicates the non-cyclic structure V while the 4th Edition indicates yet another structural isomer in which $R_2$ is O-linked rather than N-linked. In practice, a complex mixture of cyclic and non-cyclic species is likely to exist and both definitions are given here for sake of completeness. Preferred for use herein, however, are the non-cyclic species.

Examples of suitable amphoteric surfactants of type (a) include compounds of formula IV and/or V in which $R_1$ is $C_8H_{17}$ (especially iso-capryl), $C_9H_{19}$ and $C_{11}H_{23}$ alkyl. Especially preferred are the compounds in which $R_1$ is $C_9H_{19}$, Z is $CO_2M$ and $R_2$ is H; the compounds in which $R_1$ is $C_{11}H_{23}$, Z is $CO_2M$ and $R_2$ is $CH_2CO_2M$; and the compounds in which $R_1$ is $C_{11}H_{23}$, Z is $CO_2M$ and $R_2$ is H.

In CTFA nomenclature, materials suitable for use in the present invention include cocoamphocarboxypropionate, cocoamphocarboxy propionic acid, and especially cocoamphoacetate and cocoamphodiacetate (otherwise referred to as cocoamphocarboxyglycinate). Specific commercial products include those sold under the trade names of Ampholak 7TX (sodium carboxy methyl tallow polypropyl amine), Empigen CDL60 and CDR 60 (Albright & Wilson), Miranol H2M Conc. Miranol C2M Conc. N. P., Miranol C2M Conc. O. P., Miranol C2M SF, Miranol CM Special (Rhône-Poulenc); Alkateric 2CIB (Alkaril Chemicals); Amphoterge W-2 (Lonza, Inc.); Monateric CDX-38, Monateric CSH-32 (Mona Industries); Rewoteric AM-2C (Rewo Chemical Group); and Schercotic MS-2 (Scher Chemicals).

It will be understood that a number of commnercially-available amphoteric surfactants of this type are manufactured and sold in the form of electroneutral complexes with, for example, hydroxide counterions or with anionic sulfate or sulfonate surfactants, especially those of the sulfated $C_8$–$C_{18}$ alcohol, $C_8$–$C_{18}$ ethoxylated alcohol or $C_8$–$C_{18}$ acyl glyceride types. Preferred from the viewpoint of mildness and product stability, however, are compositions which are essentially free of (non-ethoxylated) sulfated alcohol surfactants. Note also that the concentrations and weight ratios of the amphoteric surfactants are based herein on the uncomplexed forms of the surfactants, any anionic surfactant counterions being considered as part of the overall anionic surfactant component content.

Examples of preferred amphoteric surfactants of type (b) include N-alkyl polytrimethylene poly-, carboxymethylamines sold under the trade names Ampholak X07 and Ampholak 7CX by Berol Nobel and also salts, especially the triethanolammonium salts and salts of N-lauryl-beta-amino propionic acid and N-lauryl-imino-dipropionic acid. Such materials are sold under the trade name Deriphat by Henkel and Mirataine by Rhône-Poulenc.

The compositions herein can also contain from about 0.1% to about 20%, more preferably from about 0.1% to about 10%, and especially from about 1% to about 8% by weight of a zwitterionic surfactant.

Water-soluble betaine surfactants suitable for inclusion in the compositions of the present invention include alkyl betaines of the formula $R_5R_6R_7N^+$ $(CH_2)_nCO_2M$ and amido betaines of the formula (IX)

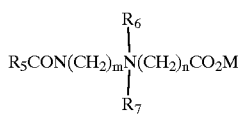

wherein $R_5$ is $C_{11}$–$C_{22}$ alkyl or alkenyl, $R_6$ and $R_7$ are independently $C_1$–$C_3$ alkyl, M is H, alkali metal, alkaline earth metal, ammonium or alkanolammonium, and n, m are each numbers from 1 to 4. Preferred betaines include cocoamidopropyldimethylcarboxymethyl betaine, laurylamidopropyldimethylcarboxymethyl betaine and Tego betaine (RTM).

Water-soluble sultaine surfactants suitable for inclusion in the compositions of the present invention include alkylamido sultaines of the formula;

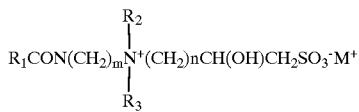

wherein $R_1$ is $C_7$ to $C_{22}$ alkyl or alkenyl, $R_2$ and $R_3$ are independently $C_1$ to $C_3$ alkyl, M is H, alkali metal, alkaline earth metal, ammonium or alkanolammonium and m and n are numbers from 1 to 4. Preferred for use herein is coco amido propylhydroxy sultaine.

Water-soluble amine oxide surfactants suitable for inclusion in the compositions of the present invention include alkyl amine oxide $R_5R_6R_7NO$ and amido amine oxides of the formula

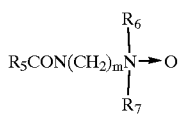

wherein $R_5$ is $C_{11}$ to $C_{22}$ alkyl or alkenyl, $R_6$ and $R_7$ are independently $C_1$ to $C_3$ alkyl, M is H, alkali metal, alkaline earth metal, ammonium or alkanolammonium and m is a number from 1 to 4. Preferred amine oxides include cocoamidopropylamine oxide, lauryl dimethyl amine oxide and myristyl dimethyl amine oxide.

Polymeric Cationic Conditioning Agent

The compositions according to the present invention can optionally include a polymeric cationic conditioning agent. Polymeric cationic conditioning agents are valuable in the compositions according to the present invention for provision of desirable skin feel attributes. The polymeric skin conditioning agent is preferably present at a level from about 0.01% to about 5%, preferably from about 0.05% to about 4%, even more preferably from about 0.01% to about 3% and especially from about 0.0% to about 2% by weight.

Suitable polymers are high molecular weight materials (mass-average molecular weight determined, for instance, by light scattering, being generally from about 2,000 to about 5,000,000, preferably from about 5,000 to about 3,000,000 more preferably from 100,000 to about 1,000,000).

Representative classes of polymers include cationic polysaccharides; cationic homopolymers and copolymers derived from acrylic and/or methacrylic acid; cationic cellulose resins; cationic copolymers of dimethyldiallylammonium chloride and acrylamide and or acrylic acid; cationic homopolymers of dimethyldiallylammonium chloride; cationic polyalkylene and ethoxypolyalkylene imines; quaternized silicones, and mixtures thereof.

By way of exemplification, cationic polymers suitable for use herein include cationic guar gums such as hydroxypropyl trimethyl ammonium guar gum (d.s. of from 0.11 to 0.22) available commercially under the trade names Jaguar C-14-S(RTM) and Jaguar C-17(RTM) and also Jaguar C-16 (RTM), which contains hydroxypropyl substituents (d.s. of from 0.8–1.1) in addition to the above-specified cationic groups, and quaternized hydroxy ethyl cellulose ethers available commercially under the trade names Ucare Polymer JR-30M, JR-400, Catanal (RTM) and Celquat. Other suitable cationic polymers are homopolymers of dimethyldiallylammonium chloride available commercially under the trade name Merquat 100, copolymers of dimethyl aninoethylmethacrylate and acrylamide, copolymers of dimethyldiallylammonium chloride and acrylamide, available commercially under the trade names Merquat 550 and Merquat S, acrylic acid/dimethyldiallylammonium chloride/acrylamide copolymers available under the trade name Merquat 3330, quaternized vinyl pyrrolidone acrylate or methacrylate copolymers of amino alcohol available commercially under the trade name Gafquat, for example Polyquaternium 11, 23 and 28 (quaternized copolymers of vinyl pyrrolidone and dimethyl aminoethylmethacrylate—Gafquat 755N and quaternized copolymers of vinyl pyrrolidone and dimethyl aminoethylmethacrylamide—HS-100), vinyl pyrrolidone/vinyl imidazolium methochloride copolymers available under the trade names Luviquat FC370, Polyquaternium 2, and polyalkyleneimines such as polyethylenimine and ethoxylated polyethylenimine.

The compositions of the invention may also contain from about 0.1% to about 20%, preferably from about 1% to about 15%, and more preferably from about 2% to about 10% by weight of an oil derived nonionic surfactant or mixture of oil derived nonionic surfactants. Oil derived nonionic surfactants are valuable in compositions according to the invention for the provision of skin feel benefits both in use and after use. Suitable oil derived nonionic surfactants for use herein include water soluble vegetable and animal-derived emollients such as triglycerides with a polyethyleneglycol chain inserted; ethoxylated mono and di-glycerides, polyethoxylated lanolins and ethoxylated butter derivatives. One preferred class of oil-derived nonionic surfactants for use herein have the general formula (XII)

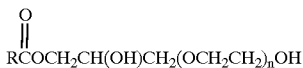

wherein n is from about 5 to about 200, preferably from about 20 to about 100, more preferably from about 30 to about 85, and wherein R comprises an aliphatic radical having on average from about 5 to 20 carbon atoms, preferably from about 7 to 18 carbon atoms.

Suitable ethoxylated oils and fats of this class include polyethyleneglycol derivatives of glyceryl cocoate, glyceryl caproate, glyceryl caprylate, glyceryl tallowate, glyceryl palmate, glyceryl stearate, glyceryl laurate, glyceryl oleate, glyceryl ricinoleate, and glyceryl fatty esters derived from triglycerides, such as palm oil, almond oil, and corn oil, preferably glyceryl tallowate and glyceryl cocoate.

Suitable oil derived nonionic surfactants of this class are available from Croda Inc. (New York, U.S.A.) under their Crovol line of materials such as Crovol EP40 (PEG 20 evening primrose glyceride), Crovol EP 70 (PEG 60 evening primrose glyceride) Crovol A-40 (PEG 20 almond glyceride), Crovol A-70 (PEG 60 almond glyceride), Crovol M40 (PEG 20 maize glyceride), Crovol M-70 (PEG 60 maize glyceride), Crovol PK-40 (PEG 12 palm kernel glyceride), and Crovol PK-70 (PEG 45 palm kernel glyceride) and under their Solan range of materials such as Solan E, E50 and X polyethoxylated lanolins and Aqualose L-20 (PEG 24 lanolin alcohol) and Aqualose W 15 (PEG 15 lanolin alcohol) available from Westbrook Lanolin. Further suitable surfactants of this class are commercially available from Sherex Chemical Co. (Dublin, Ohio, U.S.A.) under their Varonic LI line of surfactants and from Rewo under their Rewoderm line of surfactants. These include, for example, Varonic LI 48 (polyethylene glycol (n=80) glyceryl tallowate, alternatively referred to as PEG 80 glyceryl tallowate), Varonic LI 2 (PEG 28 glyceryl tallowate), Varonic LI 420 (PEG 200 glyceryl tallowate), and Varonic LI 63 and 67 (PEG 30 and PEG 80 glyceryl cocoates), Rewoderm LI5-20 (PEG-200 paimitate), Rewoderm LIS-80 (PEG-200 palmitate with PEG-7 glyceryl cocoate) and Rewoderm LIS-75 (PEG-200 palmitate with PEG-7 glyceryl cocoate) and mixtures thereof. Other oil-derived emollients suitable for use are PEG derivatives of corn, avocado, and babassu oil, as well as Softigen 767 (PEG(6) caprylic/capric glycerides).

Also suitable for use herein are nonionic surfactants derived from composite vegetable fats extracted from the fruit of the Shea Tree (Butyrospermum Karkii Kotschy) and derivatives thereof. This vegetable fat, known as Shea Butter is widely used in Central Africa for a variety of means such as soap making and as a barrier cream, it is marketed by Sederma (78610 Le Perray En Yvelines, France). Particularly suitable are ethoxylated derivatives of Shea butter available from Karlshamn Chemical Co. (Columbos, Ohio, U.S.A.) under their Lipex range of chemicals, such as Lipex 102 E-75 and Lipex 102 E-3 (ethoxylated mono, di-glycerides of Shea butter) and from Croda Inc. (New York, U.S.A.) under their Crovol line of materials such as Crovol SB-70 (ethoxylated mono, di-glycerides of Shea butter). Similarly, ethoxylated derivatives of Mango, Cocoa and Illipe butter may be used in compositions according to the invention. Although these are classified as ethoxylated nonionic surfactants it is understood that a certain proportion may remain as non-ethoxylated vegetable oil or fat.

Other suitable oil-derived nonionic surfactants include ethoxylated derivatives of almond oil, peanut oil, rice bran oil, wheat germ oil, linseed oil, jojoba oil, oil of apricot pits, walnuts, palm nuts, pistachio nuts, sesame seeds, rapeseed, cade oil, corn oil, peach pit oil, poppyseed oil, pine oil, castor oil, soybean oil, avocado oil, safflower oil, coconut oil, hazelnut oil, olive oil, grapeseed oil, and sunflower seed oil.

Oil derived nonionic surfactants highly preferred for use herein from the viewpoint of optimum mildness and skin feel characteristics are Lipex 102-3 (RTM) (PEG-3 ethoxylated derivatives of Shea Butter) and Softigen 767 (RTM) (PEG-6 caprylic/capric glycerides).

Hydrotrope

The compositions according to the present invention may contain as an optional feature a hydrotrope. Suitable for use herein as hydrotropes are those well known in the art, including sodium xylene sulphonate, ammonium xylene sulphonate, sodium cumene sulphonate, short chain alkyl sulphate and mixtures thereof. Hydrotrope may be present in the compositions according to the invention at a level of from about 0.01% to about 5%, preferably from about 0.1% to about 4%, more preferably from about 0.5% to about 3% by weight. Hydrotrope, as defined herein, means, a material which, when added to a non-dilute, water-soluble surfactant system can modify its viscosity and rheological profile.

To achieve both good product thickening and rheological attributes in non-dilute, water-soluble surfactant matrices in the presence of hydrotrope can be a challenging process. Thus it would be desirable to develop a thickening system for the delivery of both good product thickening and rheological attributes in non-dilute, water-soluble surfactant systems which comprise a hydrotrope.

Applicant has found that thickening system of the present invention is valuable for the delivery of good product thickening and rheology attributes in water-soluble, non-dilute surfactant systems comprising polyhydroxy fatty acid amide and auxiliary surfactants in the presence of hydrotrope. Applicant has also found that excellent product thickening is delivered when the ratio of total water-soluble surfactant level to total hydrotrope level is in the range of from about 5:1 to about 1:5, preferably from about 3:1 to about 1:3, more preferably from about 1.5:1 to about 1:1.5 and furthermore that a ratio of total polyhydroxy fatty acid amide surfactant level to total hydrotrope level in the range of from about 3:1 to about 1:3, preferably from about 1.5:1 to about 1:1.5, more preferably about 1:1 is especially valuable for the delivery of good thickening attributes.

According to a further aspect of the invention there is provided a personal cleansing composition comprising:

(a) from about 0.01% to about 15% by weight of a thickening system which consists essentially of associative polymer and polar oil having a required HLB of at least 12.

(b) from about 0.1% to about 20% by weight of a nonionic polyhydroxy fatty acid amide surfactant having the general formula (III):

wherein $R_8$ is $C_5$–$C_{31}$ hydrocarbyl, $R_9$ is hydrogen, $C_1$–$C_8$ alkyl or hydroxyalkyl and $Z_2$ is a polyhydroxy-hydrocarbyl moiety;

(c) from about 1% to about 60% by weight of water-soluble auxiliary surfactant other than the polyhydroxy fatty acid amide surfactant of (b), selected from anionic surfactant, nonionic, zwitterionic and amphoteric surfactants and mixtures thereof; and (d) water.

wherein the average carbon chain length of the polar oil is from about 10 to about 18 carbon atoms and is substantially similar to the average carbon chain length of the combined polyhydroxy fatty acid amide and other surfactants in the water-soluble, non-dilute surfactant matrix, and wherein the ratio of total water-soluble surfactant level to total hydrotrope level is in the range of from about 5:1 to about 1:5.

The compositions according to the present invention can also comprise lipophilic emulsifiers as skin care actives. Suitable lipophilic skin care actives include anionic food grade emulsifiers which comprise a di-acid mixed with a monoglyceride such as succinylated monoglycerides, monostearyl citrate, glyceryl monostearate diacetyl tartrate and mixtures thereof.

The compositions of the invention may also include an insoluble perfume or cosmetic oil or wax or a mixture thereof at a level up to about 20%, preferably up to about 10%, even more, preferably up to about 3% by weight wherein the oil or wax is insoluble in the sense of being insoluble in the product matrix at a temperature of 25° C. Addition of such oils or waxes can provide emolliency, mildness and rinsibility characteristics to personal cleansing compositions according to the invention. It is a feature of the invention, however, that compositions having excellent emolliency and mildness together with desirable physical attributes (clarity etc.) can be delivered which contain less than about 1%, preferably less than 0.5% by weight of an added oil phase (other than the polar oil). Physically, preferred compositions of this type take the form of an optically-clear solution or microemulsion. In compositions including an additional perfume or cosmetic oil or wax, preferably the weight ratio of oil-derived nonionic surfactant to added oil is at least about 1:2, more especially at least about 3:1.

Suitable insoluble cosmetic oils and waxes for use herein can be selected from water-insoluble silicones inclusive of non-volatile polyalkyl and polyaryl siloxane gums and fluids, volatile cyclic and linear polyalkylsiloxanes, polyalkoxylated silicones, amino and quaternary ammonium modified silicones, rigid cross-linked and reinforced silicones and mixtures thereof, $C_1$–$C_{24}$ esters of $C_8$–$C_{30}$ fatty acids such as isopropyl myristate, myristyl myristate and cetyl ricinoleate, $C_8$–$C_{30}$ esters of benzoic acid, beeswax, saturated and unsaturated fatty alcohols such as behenyl alcohol, hydrocarbons such as mineral oils, petrolatum squalane and squalene, polybutene, fatty sorbitan esters (see U.S. Pat. No. 3,988,255, Seiden, issued Oct. 26th 1976), lanolin and oil-like lanolin derivatives, animal and vegetable triglycerides such as almond oil, peanut oil, wheat germ oil, rice bran oil, linseed oil, jojoba oil, oil of apricot pits, walnuts, palm nuts, pistachio nuts, sesame seeds, rapeseed, cade oil, corn oil, peach pit oil, poppyseed oil, pine oil, castor oil, soyabean oil, avocado oil, safflower oil, coconut oil, hazelnut oil, olive oil, grapeseed oil, and sunflower seed oil, and $C_1$–$C_{24}$ esters of dimer and trimer acids such as diisopropyl dimerate, diisostearylmalate, diisostearyldimerate and triisostearyltrimerate.

The viscosity of the final composition (Brookfield DV II, 1 rpm with Cone CP41 or CP52, 25° C., neat) is preferably at least about 500 cps, more preferably from about 1,000 to about 50,000 cps, especially from about 1,000 to about 30,000 cps, more especially from about 1,000 to about 15,000 cps.

The cleansing compositions can optionally include other hair or skin moisturizers which are soluble in the cleansing composition matrix. The preferred level of such moisturizers is from about 0.5% to about 20% by weight. In preferred embodiments, the moisturizer is selected from essential amino acid compounds found naturally occurring in the stratum corneum of the skin and water-soluble nonpolyol nonocclusives and mixtures thereof.

Some examples of more preferred nonocclusive moisturizers are polybutene, squalane, sodium pyrrolidone carboxylic acid, D-panthenol, lactic acid, L-proline, guanidine, pyrrolidone, hydrolyzed protein and other collagen-derived proteins, aloe vera gel, acetamide MEA and lactamide MEA and mixtures thereof.

Compositions according to the present invention may also include an opacifier or pearlescing agent. Such materials may be included at a level of from about 0.01% to about 5%, preferably from about 0.2% to about 1.3% by weight. A suitable opacifier for inclusion in the present compositions is a polystyrene dispersion available under the trade names Lytron 621 & 631 (RTM) from Morton International.

Additional opacifiers/pearlescers suitable for inclusion in the compositions of the present invention include: titanium dioxide, $TiO_2$; EUPERLAN 810 (RTM); TEGO-PEARL (RTM); long chain ($C_{16}$–$C_{22}$) acyl derivatives such as glycol or polyethylene glycol esters of fatty acid having from about 16 to about 22 carbon atoms and up to 7 ethyleneoxy units; alkanolamides of fatty acids, having from about 16 to about 22 carbon atoms, preferably about 16 to 18 carbon atoms such as stearic monoethanolamide, stearic diethanolamide, stearic monoisopropanolamide and stearic monoethanolamide and alkyl ($C_{16}$–$C_{22}$) dimethyl amine oxides such as stearyl dimethyl amine oxide.

In preferred compositions the opacifier/pearlescer is present in the form of crystals. In highly preferred compositions the opacifier/pearlescer is a particulate polystyrene dispersion having a particle size of from about 0.05 microns to about 0.45 microns, preferably from about 0.17 microns to about 0.3 microns, such dispersions being preferred from the viewpoint of providing optimum rheology and shear-thinning behaviour. Highly preferred is styrene PVP copolymer and Lyton 631 (RTM).

A number of additional optional materials can be added to the cleansing compositions each at a level of from about 0.1% to about 2% by weight. Such materials include proteins and polypeptides and derivatives thereof; water-soluble or solubilizable preservatives such as DMDM Hydantoin, Germall 115, methyl, ethyl, propyl and butyl esters of hydroxybenzoic acid, EDTA, Euxyl (RTM) K400, natural preservatives such as benzyl alcohol, potassium sorbate and bisabalol; sodium benzoate and 2-phenoxyethanol; other moisturizing agents such as hyaluronic acid, chitin, and starch-grafted sodium polyacrylates such as Sanwet (RTM) IM-1000, IM-1500 and IM-2500 available from Celanese Superabsorbent Materials, Portsmith, Va., U.S.A. and described in U.S. Pat. No. 4,076,663; solvents ; suitable anti-bacterial agents such as Oxeco (phenoxy isopropanol), Trichlorocarbanilide (TCC) and Triclosan and; low temperature phase modifiers such as ammonium ion sources (e.g. $NH_4$ Cl); viscosity control agents such as magnesium sulfate and other electrolytes; colouring agents; $TiO_2$ and $TiO_2$— coated mica; perfumes and perfume solubilizers; and zeolites such as Valfour BV400 and derivatives thereof and $Ca^{2+}/Mg^{2+}$ sequestrants such as polycarboxylates, amino polycarboxylates, polyphosphonates, amino polyphosphonates, EDTA etc, water softening agents such as sodium citrate and insoluble particulates such as zinc stearate and fumed silica. Water is also present at a level preferably of from about 5% to about 99.89%, preferably from about 40% to about 90%, more preferably at least about 80% by weight of the compositions herein.

The pH of the compositions is preferably from about 4 to about 10, more preferably from about 5 to about 9, especially from about 6 to about 8.

EXPERIMENTAL RESULTS

All viscosities are measured in mPa.s (cps) at 26.7° Celcius.

All level mentioned below are percentages weight by weight.

Method:

Brookfield Cone & Plate Model DV II with Spindle CP41.

Measurements are performed at 1 rpm or at the appropriate speed to get the correct torque value. All measurements are given ±50 cps

SURFACTANT SYSTEM:

Anionic (Sodium C12-13 Pareth-5 Carboxylate), Sodium Decyl Sulphate (Empicol LC 35); Nonionic (C12–14 N-Methyl Glucose Amide); Amphoteric (Cocoamphodiacetate).

Total level of surfactants: 12% by weight.

TABLE I

Interaction between associative polymers and polar oil

| Polymer | Level | Polar Oil | Level | Viscosity (cps) |
|---|---|---|---|---|
| Natrosol Plus 430 | 0.5 | C12–13 Alcohol | 0.0 | 350 |
| Natrosol Plus 430 | 0.0 | C12–13 Alcohol | 0.6 | 350 |
| Natrosol Plus 430 | 0.5 | C12–13 Alcohol | 0.6 | 3,500 |
| Acrysol 44 | 0.5 | C12–13 Alcohol | 0.0 | 150 |
| Acrysol 44 | 0.0 | C12–13 Alcohol | 0.6 | 350 |
| Acrysol 44 | 0.5 | C12–13 Alcohol | 0.6 | 1,000 |

TABLE II

Effect of degree (X) of ethoxylation of polar oil

| Polymer | Level | Polar Oil | Level | Viscosity (cps) |
|---|---|---|---|---|
| Acrysol 44 | 1.0 | C12–14 0 EO (Laurex NC) | 0.7 | 1,200 |
| Acrysol 44 | 1.0 | C12–14 3 EO (Genapol L3) | 0.7 | 300 |
| Acrysol 44 | 1.0 | C12–14 7 EO (Empicol KBE 7) | 0.7 | 50 |

The compositions according to the present invention are illustrated by the following non-limiting examples. In the examples, all concentrations are on a 100% active basis and the abbreviations have the following designation:

| | |
|---|---|
| Anionic 1 | Sodium $C_{12}$–$C_{13}$ Pareth-4-carboxylate (the sodium salt derived from the alykl ether carboxylic acid NEODOX 23-4 from Shell US Inc.) |
| Anionic 2 | Sodium Laureth-4 Carboxylate |
| Anionic 3 | Sodium decyl alkyl suplhate |
| Anionic 4 | Sodium Laureth-2 sulphate |
| Amphoteric | Disodium Cocoamphodiacetate |
| Betaine | Cocoamidopropylbetaine. |
| Nonionic | Polyhydroxy fatty acid amide of formula IX in which $R_8$ is $C_{11}$–$C_{17}$ alkyl, $R_9$ is methyl, and $Z_2$ is $CH_2(CHOH)_4CH_2OH$ |

-continued

| | |
|---|---|
| HEUR 1 | Acrysol 44. |
| HEUR 2 | Bermodol 2130 |
| HMHEC 1 | Natrosol Plus 430 |
| HMHEC 2 | Polysurf 67 |
| HNP | Glucamate DOE |
| Polar Oil 1 | Dobanol 23 |
| Polar Oil 2 | Laurex NC/E |

EXAMPLES I to VIII

The following are personal cleansing compositions in the form of shower gel or bath foam products and which are representative of the present invention:

| | I | II | III | IV | V | VI | VII | VIII |
|---|---|---|---|---|---|---|---|---|
| Anionic 1 | 4.0 | 6.0 | 4.0 | 3.0 | — | — | — | — |
| Anionic 2 | — | — | — | — | 4.0 | 6.0 | — | — |
| Anionic 3 | 2.0 | 3.0 | 1.5 | 2.5 | 3.0 | — | — | — |
| Anionic 4 | — | — | — | — | — | 3.0 | 12.0 | 8.0 |
| Amphoteric | 1.0 | 1.0 | 0.5 | 0.2 | 1.0 | 1.0 | — | — |
| Betaine | — | — | .3 | — | — | — | 3.0 | 3.0 |
| Nonionic | 4.0 | 2.0 | 2.5 | 3.0 | 3.0 | 2.0 | 0.5 | 5.0 |
| HEUR 1 | 0.7 | — | — | — | 1.0 | 0.5 | — | — |
| HEUR 2 | — | — | — | 0.6 | — | — | 0.5 | — |
| HMHEC 1 | — | 0.5 | — | — | — | — | — | — |
| HMHEC 2 | — | — | 0.8 | — | — | 0.5 | — | 0.5 |
| HNP | — | — | — | 0.5 | — | — | — | — |
| Polar Oil 1 | 0.6 | 0.3 | 0.5 | 1.0 | — | — | 0.3 | 0.8 |
| Polar Oil 2 | — | — | — | — | 0.4 | 0.6 | — | — |
| Water | | | | to 100 | | | | |

Compositions I to VIII can be prepared by firstly dispersing the water-soluble or colloidally water-soluble associative polymer in water at up to about 70° C. either in a Tri-blender (TM) or by extended stirring and hydration. The surfactants are added to this mixture with mild agitation (continued heating at up to about 70° C. can be used). It is preferable to add the polar oil following the surfactants. Skin care agents (where present) can then be added along with the remaining water-soluble, oil-insoluble ingredients and finally the remaining water, preservative, opacifier and perfume are added.

The compositions have a viscosity (Brookfield DV II, 1 rpm with Cone CP41 or CP52, 25° C., neat) in the range of from 500 to 50,000 cps, preferably from 1,000 to 15,000 cps.

The products provide excellent product thickening and rheological attributes, in storage, in dispensing and in-use, in combination with good efficacy benefits including excellent rinsibility, mildness, skin conditioning, skin moisturising, good product stability, cleansing and lathering.

What is claimed is:

1. A liquid personal cleansing composition comprising:

(a) from about 0.01% to about 15% by weight of a thickening system which consists essentially of hydrophobically modified water-soluble associative polymer and polar oil having a required HLB of at least 12 wherein the polar oil is present at a level of from about 0.01% to about 3% and wherein the polar oil is selected from the group consisting of natural primary fatty alcohols and synthetic primary fatty alcohols;

(b) from about 0.1% to about 20% by weight of a nonionic polyhydroxy fatty acid amide surfactant having the general formula (II):

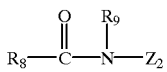

wherein $R_8$ is $C_5$–$C_{31}$ hydrocarbyl, $R_9$ is hydrogen, $C_1$–$C_8$ alkyl or hydroxyalkyl and $Z_2$ is a polyhydroxyhydrocarbyl moiety;

(c) from about 1% to about 60% by weight of water-soluble auxiliary surfactant other than the polyhydroxy fatty acid amide surfactant of (b), selected from anionic surfactant, nonionic, zwitterionic and amphoteric surfactants and mixtures thereof; and (d) waters, wherein the polar oil has an average carbon chain length of from about 12 to about 18 carbon atoms and is substantially similar to the average carbon chain length of the combined polyhydroxy fatty acid amide and other surfactants in the water-soluble, non-dilute surfactant matrix.

2. A composition according to claim 1 wherein the total level of the thickening system is from about 0.01% to about 10% by weight.

3. A composition according to claim 2 wherein the ratio of associative polymer to polar oil is in the range of from about 1:5 to about 5:1.

4. A composition according to claim 3 wherein associative polymer is present at a level of from about 0.05% to about 8%.

5. A composition according to claim 1 wherein the associative polymer has an average molecular weight in the range of from about 10,000 to about 1,000,000.

6. A composition according to claim 5 wherein the hydrophobically modified water-soluble associative polymer is selected from the group consisting of hydrophobically modified hydroxyalkyl cellulose polymers, hydrophobically modified alkoxylated urethane polymers, hydrophobically modified nonionic polyols and mixtures thereof.

7. A composition according to claim 1 wherein the polar oil has a required HLB value of from about 12 to about 15.

8. A composition according to claim 1 wherein the polar oil is lauryl alcohol.

9. A composition according to claim 1 wherein the composition has a viscosity (Brookfield DV-II, 1 rpm with Cone CP41 or CP52, 25° C., neat) in the range from 500 to 50,000 cps,.

10. A composition according to claim 1 wherein the polyhydroxy fatty acid amide has the formula $R_8(CO)N(CH_3)CH_2(CHOH)_4CH_2OH$ wherein $R_8$ is a $C_6$–$C_{19}$ straight chain alkyl or alkenyl group.

11. A composition according to claim 1 wherein the total level of auxiliary water-soluble surfactant, other than the polyhydroxy fatty acid amide of (b), is from about 2% to about 40%.

12. A composition according to claim 1 wherein the auxiliary, water-soluble anionic surfactant is selected from the group consisting of alkyl sulphates, ethoxylated alkyl sulfates, alkyl glyceryl ether sulfonates, methyl acyl taurates, fatty acyl glycinates, alkyl ethoxy carboxylates, N-acyl glutamates, acyl isethionates, alkyl sulfosuccinates, alkyl ethoxy sulphosuccinates, alpha-sulfonated fatty acids, their salts and/or their esters, alkyl phosphate esters, ethoxylated alkyl phosphate esters, acyl sarcosinates and fatty acid/protein condensates, and mixtures thereof.

13. A composition according to claim 12 wherein the auxiliary, water-soluble anionic surfactant is selected from the group consisting of alkyl sulfate, ethoxylated alkyl sulphate, alkyl ethoxy carboxylate and mixtures thereof.

14. A composition according to claim 1 which additionally comprises from about 0.1% to about 20% by weight of an auxiliary, water-soluble nonionic surfactant selected from the group consisting of $C_{12}$–$C_{14}$ fatty acid mono-and di-ethanolamides and ethoxylated derivatives thereof, sucrose polyester surfactants, $C_{10}$–$C_{18}$ alkyl polyglycosides and mixtures thereof.

15. A composition according to claim 1 wherein the amphoteric surfactant is selected from the group consisting of surfactants of formula IV, surfactants of formula V, and mixtures thereof.

16. A composition according to claim 1 wherein the auxiliary, water-soluble zwitterionic surfactant is selected from the group consisting of alkyl betaine, amido betaine, alkyl amido sultaine and mixtures thereof.

17. A composition according to claim 1 further comprising a polymeric cationic conditioning agent having a mass average molecular weight in the range from about 2000 to about 5,000,000.

18. A composition according to claim 17 wherein the polymeric cationic conditioning agent is selected from the group consisting of cationic polysaccharides; cationic homopolymers and copolymers derived form acrylic and/or methacrylic acid; cationic cellulose resins; cationic copolymers of dimethyidiallylammonium chloride and acrylic acid; cationic homopolymers of dimethyidiallylammonium chloride; cationic polyalkylene and ethoxypolyalkylene imines; quaternized silicones, and mixtures thereof.

19. A composition according to claim 18 wherein the polymeric cationic conditioning agent is present at a level of from about 0.05% to about 4% by weight.

20. A composition according to claim 1 further comprising from about 0.1% to about 20% by weight of nonionic surfactant selected from the group consisting of ethoxylated oils and fats having the formula (XII)

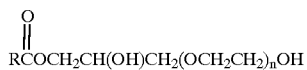

wherein n is from about 5 to 200, and wherein R comprises an aliphatic radical having an average from about 5 to 20 carbon atoms.

21. A composition according to claim 1 further comprising up to about 20% by weight of perfume or cosmetic oil.

22. A composition according to claim 1 further comprising hydrotrope at a level of from about 0.01% to about 5% by weight.

23. A composition according to claim 1 wherein the water-soluble auxiliary amphoteric surfactant is selected from the group consisting of:

(a) a member selected from the group consisting of: surfactants of formula (IV)

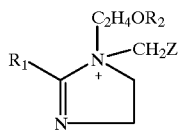

wherein $R_1$ is $C_7$–$C_{22}$ alkyl or alkenyl, $R_2$ is hydrogen or $CH_2Z$, each Z is independently $CO_2$ or $CH_2$ $CO_2M$, and M is H, alkali metal, alkaline earth metal, ammonium or alkanolammonium;

surfactants of formula (V)

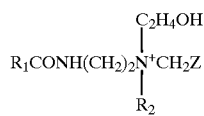

wherein $R_1$, $R_2$ and Z are as defined above; and
mixtures thereof;
(b) a member selected from the group consisting of:
aminoalkanoates of formula (VI)

wherein n, m, p, and q are numbers from 1 to 4, and $R_1$ and M are independently selected from the groups specified above;
iminodialkanoates of formula (VIII)

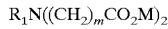

wherein n, m, p, and q are numbers from 1 to 4, and $R_1$ and M are independently selected from the groups specified above;

iminopolyalkanoates of formula (VIII)

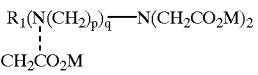

wherein n, m, p, and q are numbers from 1 to 4, and $R_1$ and M are independently selected from the groups specified above; and mixtures thereof; and
(c) mixtures thereof.

* * * * *